US00PP37711P3

(12) United States Plant Patent
Skotak, Jr.

(10) Patent No.: US PP37,711 P3
(45) Date of Patent: Sep. 22, 2026

(54) ***AECHMEA* PLANT NAMED 'A4006'**

(50) Latin Name: *Aechmea fasciata*
Varietal Denomination: A4006

(71) Applicant: Chester Skotak, Jr., Alajuela (CR)

(72) Inventor: Chester Skotak, Jr., Alajuela (CR)

( * ) Notice: Subject to any disclaimer, the term of this patent is extended or adjusted under 35 U.S.C. 154(b) by 0 days.

(21) Appl. No.: 19/401,699

(22) Filed: Nov. 26, 2025

(65) Prior Publication Data

US 2026/0157249 P1 Jun. 4, 2026

(30) Foreign Application Priority Data

Nov. 29, 2024 (QZ) ..... PBR 2024/2860

(51) Int. Cl.
*A01H 5/02* (2018.01)
*A01H 5/12* (2018.01)
*A01H 6/22* (2018.01)

(52) U.S. Cl.
USPC ..... Plt./370
CPC ..... *A01H 6/22* (2018.05); *A01H 5/02* (2013.01); *A01H 5/12* (2013.01)

(58) Field of Classification Search
USPC ..... Plt./263.1, 370
See application file for complete search history.

(56) References Cited

U.S. PATENT DOCUMENTS

PP12,685 P2 * 6/2002 Bak ..... A01H 5/02
Plt./370

* cited by examiner

*Primary Examiner* — Karen M Redden
(74) *Attorney, Agent, or Firm* — James R. Holm; Plant Novelty Rights, LLC

(57) ABSTRACT

A new and distinct *Aechmea* plant named 'A4006' particularly distinguished by leaves entirely lacking marginal spines; a very compact rosette plant habit, upright inflorescence, positioned well above the foliage; a uniform plant form and high stability through asexual propagation; distinctive bright pink bracts with violet-blue flowers.

4 Drawing Sheets

Figure 1:
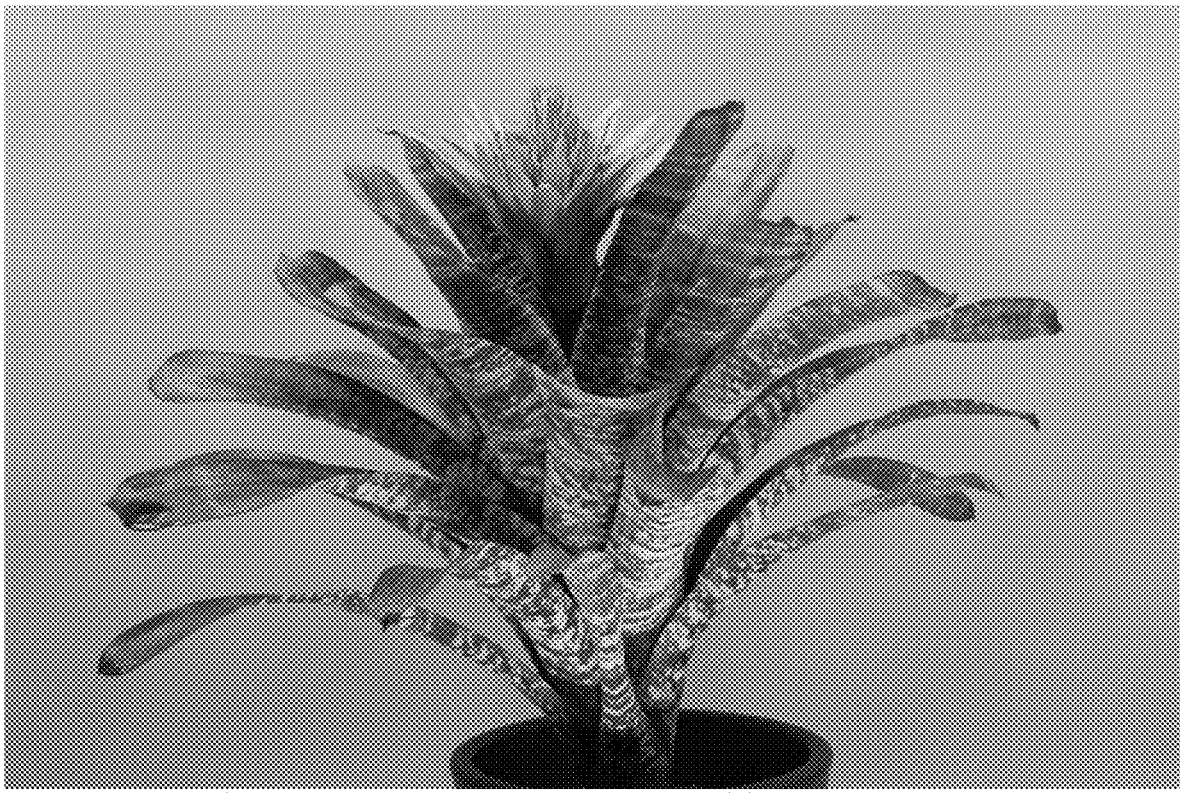

Genus and species: *Aechmea fasciata.*
Variety denomination: *'A*4006'.

STATEMENT REGARDING PRIOR DISCLOSURES BY THE INVENTOR

This application claims priority to CPVO application no. 2024/2860 filed on Nov. 29, 2024, which is herein incorporated by reference. The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period prior to the effective filing date.

BACKGROUND OF THE NEW PLANT

The present invention comprises a new and distinct variety of *Aechmea* plant, botanically known as *Aechmea fasciata*, and hereinafter referred to by the variety name 'A4006'.

*Aechmea* comprises a genus of more than 168 species of evergreen perennials suitable for cultivation in the home or in the greenhouse. *Aechmea* may be terrestrial or epiphytic. For the most part, the species vary in diameter from 12 to 18 inches to 3 or 4 feet and have rosettes of spiny-edged leaves.

Flowers and bracts of *Aechmea* frequently have brilliant colors and may last for several months. The range of colors for *Aechmea* is generally from the yellow through orange but may also include pink, orange, red and red-purple. Tubular, three-petalled flowers may also appear but are usually short-lived.

*Aechmea* may be grown as pot plants for greenhouse or home use. Typically, the plants are shaded from direct sunlight; and the central, vaselike part of the leaf rosette is normally filled with water.

*Aechmea* is native to tropical America. Leaves of *Aechmea* are usually formed from basal rosettes which are entire and in several vertical ranks. *Aechmea* has terminal spikes or panicles which are often bracted with petals united in a tube longer than the calyx.

Asexual propagation of *Aechmea* is frequently done through meristematic tissue culture. Propagation can also be from offshoots which can be detached from the mother plant and grown in an appropriate soil or bark mixture. Methods for cultivating and crossing of *Aechmea* are well known.

The new *Aechmea* variety 'A4006' is the product of a controlled cross pollination conducted by the inventor in Alajuela, Costa Rica. The objective of the breeding program was to develop compact, spineless, and uniform *Aechmea fasciata* plants suitable for pot production with upright inflorescence and improved ornamental presentation. The female or seed parent was an unnamed and unpatented *Aechmea fasciata* breeding line. The male or pollen parent was an unnamed and unpatented *Aechmea fasciata* breeding line. 'A4006' was selected by the inventor in 2021 in Alajuela, Costa Rica as a single flowering plant from within the progeny of the stated cross.

The new *Aechmea* cultivar 'A4006' was first reproduced asexually by meristematic tissue culture at a commercial laboratory in Evergem, Belgium. Asexual propagation by meristematic tissue culture of the new variety has shown that the unique features of the new variety are stable and reproduced true-to-type to date through successive generations.

SUMMARY OF THE INVENTION

The new *Aechmea* cultivar 'A4006' has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new *Aechmea* cultivar. The combination of these characteristics distinguishes 'A4006' as a new and distinct variety of *Aechmea*.

1. *Aechmea* 'A4006' exhibits leaves entirely lacking in marginal spines.
2. *Aechmea* 'A4006' exhibits a very compact rosette plant habit.
3. *Aechmea* 'A4006' exhibits a fully upright inflorescence, positioned well above the foliage.
4. *Aechmea* 'A4006' exhibits a uniform plant form and high stability through asexual propagation.
5. *Aechmea* 'A4006' exhibits distinctive bright pink bracts with violet-blue flowers.

DESCRIPTION OF THE PHOTOGRAPHS

This new *Aechmea* cultivar is illustrated by the accompanying-colored photographs which show the overall appearance and distinct characteristics of the plant. The colors shown are as true as can be reasonably obtained by conventional photographic procedures. The photographs are of 24 to 28-month-old plants grown in 14-centimeter circular containers in a conventional glass greenhouse in Evergem, Belgium. Colors in the photographs may differ slightly from the color values cited in the botanical description which accurately describes the colors of the new variety.

FIG. 1. shows the overall plant form, foliage, and inflorescence of 'A4006'.

Figure 2:
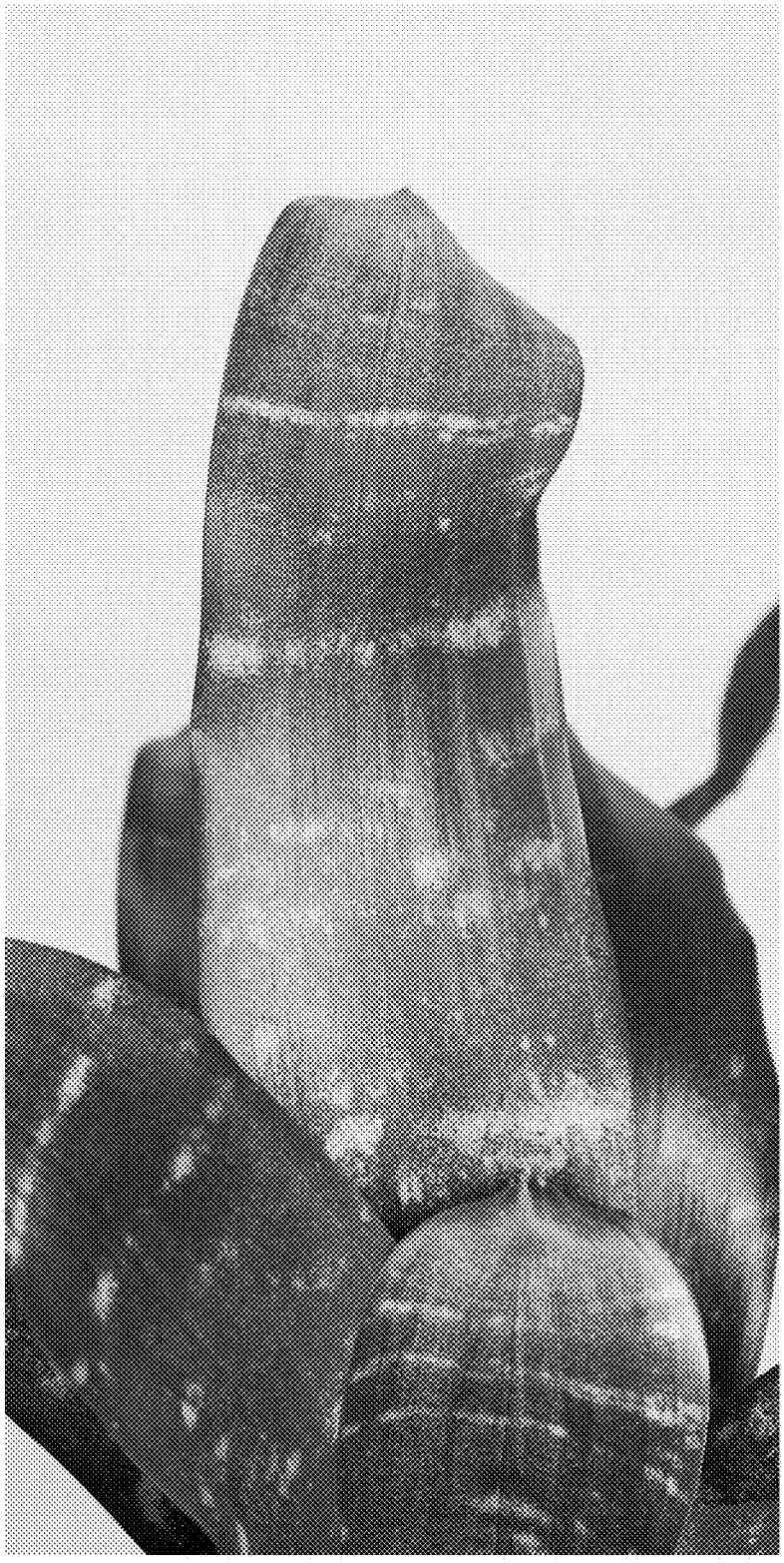

FIG. 2. shows a close-up of typical foliage observed on plants of 'A4006'.

Figure 3:
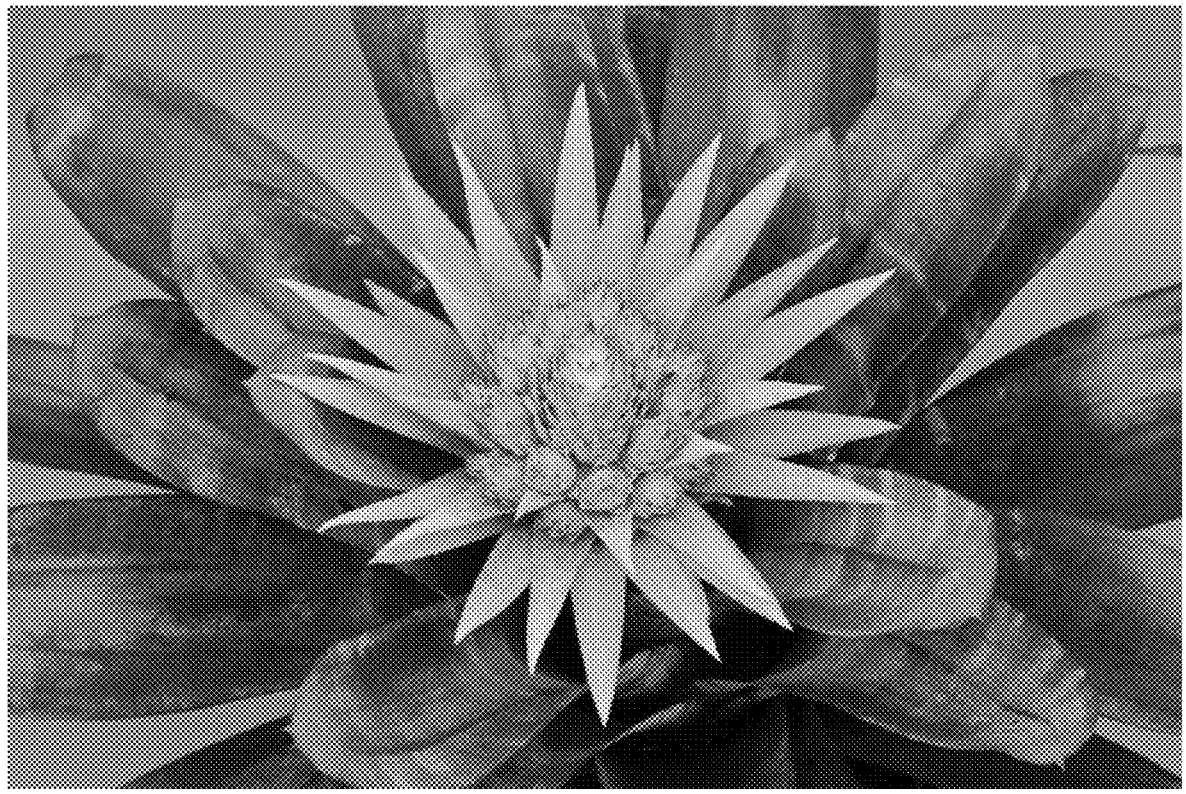

FIG. 3. shows an overhead view of a typical inflorescence observed on plants of 'A4006'.

Figure 4:
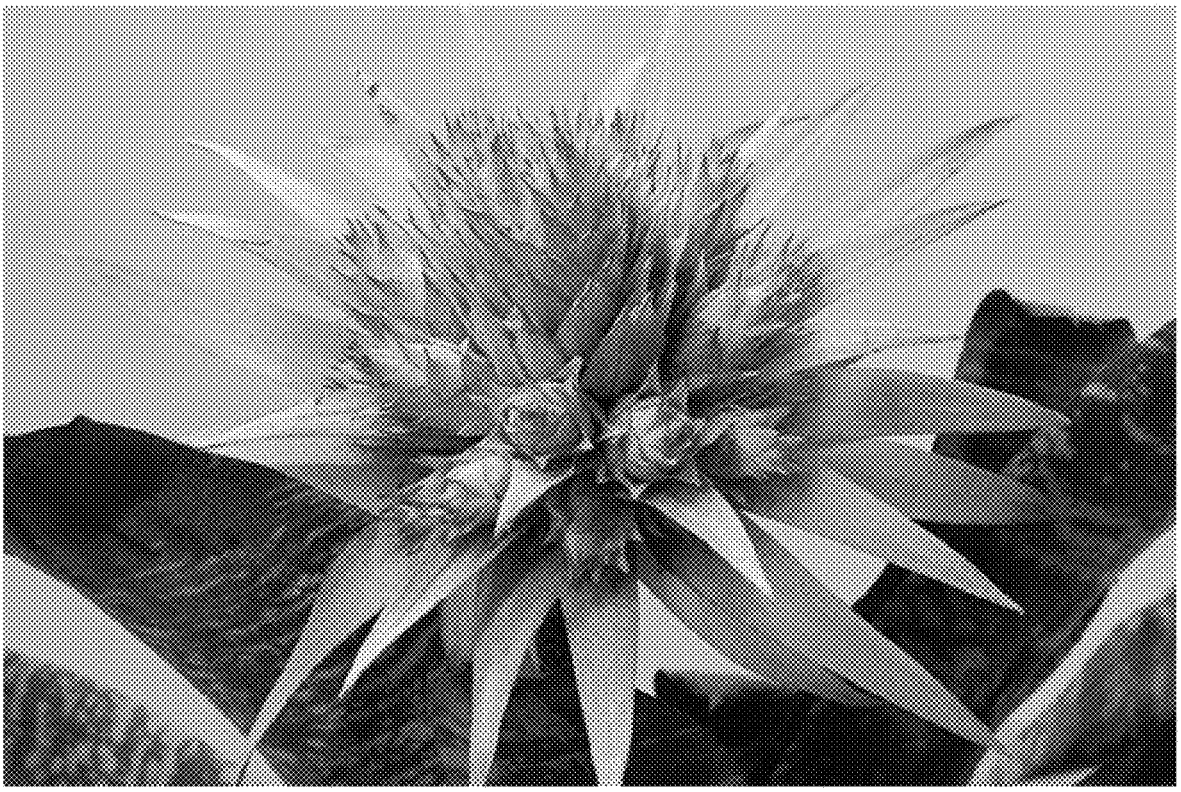

FIG. 4. shows a side view of a typical inflorescence observed on plants of 'A4006'.

DESCRIPTION OF THE NEW VARIETY

In the following description, color references are made to The Royal Horticultural Society Colour Chart, Sixth Edition, except where general color terms of ordinary dictionary significance are used.

The following observations and measurements describe plants grown in a commercial greenhouse located in Evergem, Belgium under normal light levels with no supplemental lighting. Average daily temperatures ranged between 21° C. and 23° C. and average nightly temperatures ranged between 19° C. and 21° C. Measurements and numerical values represent averages of typical plant types.

DETAILED BOTANICAL DESCRIPTION

Classification:

*Family*.—Bromeliaceae.

*Botanical*.—*Aechmea fasciata*.

*Denomination*.—'A4006'.

General description:

*Plant type*.—Tropical perennial suitable as an indoor potted plant.

*Growth habit*.—Highly symmetrical, compact and dense basal rosette; inflorescence grows from the center of the basal rosette.

*Overall plant shape*.—Flattened obovate with inflorescence carried well above the foliar plane.

*Height from soil level to top of foliar plane*.—Average 27.0 cm.

*Plant diameter or area of spread*.—Average 40.4 cm.

*Growth rate*.—Moderate.

*Plant vigor*.—Moderate.

*Branching habit*.—No lateral branching; leaves in a basal rosette, inflorescence grows from the center of the basal rosette.

*Propagation type*.—Meristematic tissue culture.

Root description:

*General*.—Slightly fleshy and very slightly fibrous.

*Length*.—Average 5.4 cm.

*Width*.—Average 0.1 cm.

*Color*.—165B (greyed-orange).

Foliage description:

*Arrangement*.—Rosulate.

*Compound or single*.—Single.

*Quantity of leaves per rosette*.—Average 21.

*Lamina*.—Shape: Oblong. Length: Average 21.3 cm. Width: Average 4.5 cm . Aspect: Slightly concave, curled downward on average. Apex shape: Truncate to broadly retuse with a mucronulate tip. Base: Sheathing. Sheath length: Average 6.1 cm. Sheath width Average 5.1 cm. Sheath color: 148C (yellow-green) and lighter towards the edge, 144B (yellow-green). Margin: Entire, spinless. Undulation: Coarsely undulate and slightly twisted axially. Lobes: Unlobed. Texture (both upper and lower surfaces): Smooth and glabrous. Rugosity: Non-rugose. Pubescence: No pubescence present. Luster: Upper surface: Glossy. Lower surface: Slightly glossy. Color: Juvenile foliage: Upper surface: 147A (yellow-green) with edges colored NN137B (green) and heavily blotched lighter than NN155D (white) with a silvery haze loosely arranged in radial lines across the lamina. Lower surface: NN137A (green) with lighter edges colored 137B (green) and heavily blotched lighter than NN155D (white) with a silvery haze loosely arranged in radial lines across the lamina. Mature foliage: Upper surface: NN137A (green) and blotched NN155D (white) with a silvery haze loosely arranged in radial lines across the lamina; significantly less white blotching on the upper half of the lamina on mature leaves. Lower surface: 147A (yellow-green) and heavily blotched lighter than NN155D (white) with a silvery haze loosely arranged in radial lines across the lamina. Venation: Pattern: Parallel. Color (mature foliage):

Upper surface: Upper surface venation is colored the same as the upper surface of the lamina. Lower surface: Lower surface venation is colored the same as the lower surface of the lamina.

Inflorescence description:

*Arrangement*.—Terminal panicle.

*Type and form*.—Panicle, consisting of a main panicle and an average of 7 secondary panicles, each consisting of an average of 10 individual flowers.

*Height*.—Average 9.0 cm, excluding peduncle.

*Diameter*.—Average 9.5 cm.

*Quantity of flowers per inflorescence*.—Average 11.

*Quantity of flowers and flower buds per plant*.—Average 75.

*Natural flowering season*.—Continuously.

*Time to flower or response time*.—6 months.

*Flower bud*.—Length: Average 2.1 cm. Diameter: Average 0.7 cm. Shape: Elliptic to oblong. Texture: Smooth and glabrous. Luster: Matte. Color: 91B (violet-blue) and fading to N88B (violet-blue) at the margins of juvenile petals, juvenile sepals colored 55D (red) and fading 155A (white) and 158D (yellow-white) towards the base.

*Flower*.—Type and form: single, rotate. Aspect: Upright to slightly outward. Habit: Freely flowering. Fragrance: Not fragrant. Shape: Rotate, petals not opening but remaining in oblanceolate shape. Vertical height: Average 0.7 cm. Horizontal diameter: Average 0.7 cm. Length (depth): Average 3.0 cm. Texture (both sides): Smooth and glabrous. Longevity: Average 4 weeks. Persistence: Persistent.

*Petals*.—Arrangement: Rotate. Quantity per flower: Average 3.Number of petal whorls: Average 1.Petal fusion: Not fused. Length: Average 2.3 cm. Width: Average 0.5 cm. Shape: Narrow oblong, concave. Tip: Obtuse. Base: Cuneate. Margin: Entire. Margin undulation: Not undulated. Texture (both upper and lower surfaces): Smooth and glabrous. Rugosity (both upper and lower surfaces): Non-rugose. Luster (both upper and lower surfaces): Very slightly glossy. Color, when opening: Upper surface: 63A (red-purple), fading transparent N155A (white) towards the base. Lower surface: 58B (red-purple), fading transparent N155A (white) towards the base. Color when fully opened: Upper surface: 63A (red-purple), fading transparent N155A (white) towards the base. Lower surface: 58B (red-purple), fading transparent N155A (white) towards the base. Venation: Inconspicuous. Petaloids: Not present.

*Sepals*.—Arrangement: Rotate. Quantity per flower: Average 3. Quantity of sepal whorls: Average 1. Length: Average 1.2 cm. Width: Average 0.7 cm. Sepal fusion: Not fused. Shape: Broad oblong, concave. Apex or tip: Bluntly acute. Base: Cuneate. Margin: Entire. Texture (both upper and lower surface): Smooth and glabrous. Luste: Upper surface: Very slightly glossy. Lower surface: Moderately glossy. Color when opening: Upper surface: Transparent 155B (white), tinged 56A (red) near the apex. Lower surface: Transparent 155C (white), tinged 55D (red) near the apex. Color when fully opened: Upper surface: Transparent 155B (white), tinged 56B (red) near the apex. Lower surface: Transparent 155C (white), tinged 55D and 56A (red) near the apex. Sepal spurs: Not present.

*Peduncle*.—Length: Average 27.4 cm Diameter: Average 1.1 cm. Shape in cross section: Round. Orientation: Vertical. Strength: Strong. Texture: Covered with a matte felt, colored 155C (white). Luster: Slightly glossy but covered with a matte felt. Color: 144C (yellow-green). Pedicels: Not present.

*Scape bracts*.—General description: Scape bracts are present along and at the top of the peduncle of the main panicle and at the base of the secondary panicle. Shape: Ovate. Length: Average 7.0 cm. Width: Average 3.1 cm. Luster: Upper surface: Slightly glossy. Lower surface: Very slightly glossy. Margin: Entire. Apex: Acute with a sharp mucronate tip; narrow apiculate on upper bracts. Base: Broad cuneate. Color: Upper surface: 62A (red-purple); lower bracts tipped 143D (green). Lower surface: 58D (red-purple) and slightly blotched NN155C (white); lower bracts tipped 143C (green).

*Floral bracts*.—General description: Below each spike of individual flowers, a single floral bract is present. Shape: Ovate and strongly concave. Length: Average 3.2 cm. Width: Average 1.4 cm. Luster: Upper surface: Slightly glossy. Lower surface: Very slightly glossy. Margin: Entire to sparsely sharp serrate. Apex: Long apiculate with a sharp tip. Base: Cuneate. Color: Upper surface: 55B (pink), tipped 55A (pink) and fading 158D (yellow-white) at the base. Lower surface: 55B (pink), tipped 55A (pink) and fading 158D (yellow-white) at the base; lower surface covered with a felt, 155C (white).

Reproductive organs:

*Quantity of stamens per flower*.—Average 6.

*Filament*.—Average 1.6 cm. Color: NN155A.

*Anther*.—Shape: Dorsifixed, narrow elliptic. Length: Average 0.4 cm. Width: Average 0.1 cm. Color: 155B (white).

*Pollen amount*.—Low.

*Pistil*.—Quantity: 1. Length: Average 2.4 cm.

*Stigma*.—Shape: Cleft shaped, three parted and fringed. Length: Average 0.2 cm. Diameter: Average 0.1 cm. Color: NN155B (white).

*Style*.—Length: Average 2.2 cm. Color: NN155D (white).

*Ovary color*.—Nearest to 155B (white).

Fruit and seed set: None observed to date.

Temperature tolerances: USDA Zones 10 to 13; at least tolerant of temperatures to 40 degrees Celsius.

Rain tolerance: High.

Wind tolerance: High.

Disease and pest tolerance: No claims are made to any superior disease or insect resistance or tolerance.

COMPARISON WITH THE PARENT PLANTS

The new *Aechmea* cultivar 'A4006' can be distinguished from its female or seed parent in the following characteristics described in Table 1 below.

TABLE 1

| Characteristic | 'A4006' | Female parent |
|---|---|---|
| Overall plant size | Smaller, compact rosette | Larger, open rosette |
| Leaf margin | Entirely spineless | Finely spined |

TABLE 1-continued

| Characteristic | 'A4006' | Female parent |
|---|---|---|
| Leaf color | Green with a stronger silver hue | Green-grey with faint silver banding |
| Leaf shape | Broad, slightly recurved | Narrow, arching |
| Inflorescence position | Fully upright above foliage | Partly within rosette |
| Floral bract color | Bright pink | Pale pink |
| Growth habit | Dense and upright | Open and spreading |

The new *Aechmea* cultivar 'A4006' can be distinguished from its male or pollen parent in the following characteristics described in Table 2 below.

TABLE 2

| Characteristic | 'A4006' | Male Parent |
|---|---|---|
| Plant size | Small and compact | Medium to large |
| Leaf margin | Spineless | Short spines |
| Leaf variegation | Subtle silver hue | Moderate |
| Inflorescence position | Fully upright | Slightly inclined |
| Floral bract color | Bright pink | Light pink |
| Flower arrangement | Dense, centered cluster | Looser |

TABLE 2-continued

| Characteristic | 'A4006' | Male Parent |
|---|---|---|
| Overall presentation | Highly symmetrical | Less symmetrical |

COMPARISON WITH RELATED KNOWN VARIETY

The new *Aechmea* cultivar 'A4006' can be distinguished from the related known variety and wild species of *Aechmea fasciata* in the following characteristics described in Table 3 below.

TABLE 3

| Characteristic | 'A4006' | *Aechmea fasciata* wild species |
|---|---|---|
| Leaf margin spines | Absent | Present |
| Growth habit | Symmetrical and compact | Loosely arranged foliage and less compact |
| Inflorescence orientation | Upright and above foliar plane | Less vertical and below foliar plane |

What is claimed is:

1. A new and distinct cultivar of *Aechmea* plant named 'A4006', substantially as illustrated and described herein.

* * * * *